(12) United States Patent
Doenges et al.

(10) Patent No.: US 6,395,881 B1
(45) Date of Patent: May 28, 2002

(54) SEPARATION OF ANTITHROMBIN III α AND β VARIANTS BY CYCLODEXTRIN-MODIFIED MICELLAR ELECTROKINETIC CHROMATOGRAPHY

(75) Inventors: Reiner Doenges, Lahntal-Caldern; Juergen Roemisch, Marburg; Harald Stauss, Dautphetal, all of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/849,257

(22) Filed: May 7, 2001

(30) Foreign Application Priority Data

May 8, 2000 (EP) ............................................ 00109182

(51) Int. Cl.$^7$ ......................... A61K 35/14; A61K 38/48; C12N 9/74

(52) U.S. Cl. .................... 530/393; 435/214; 424/94.64; 530/412; 530/413

(58) Field of Search ................................ 530/393, 412, 530/413; 435/214; 424/94.64

(56) References Cited

FOREIGN PATENT DOCUMENTS

| WO | WO96/22524 | 7/1996 |
|---|---|---|
| WO | WO97/04308 | 2/1997 |
| WO | WO97/11363 | 3/1997 |

OTHER PUBLICATIONS

Nishi, H., et al., "Micellar Electrokinetic Chromatography Perspectives in Drug Analysis", *Journal of Chromatography A* 735(1):3–27, 1996.

Tanaka, Y., et al., "Separation of Neutral and Basic Enantiomers by Cyclodextrin Electrokinetic Chromatography Using Anionic Cyclodextrin Derivatives as Chiral Pseudo-Stationary Phases", *J. High Resol. Chromatogr.* 19:(8)421–433, Aug. 1996.

E. Szökö, "Protein and Peptide Analysis by Capillary Zone Electrophoresis and Micellar Electrokinetic Chromatography", *Electrophoresis* 18:74–81, 1997.

M. Petersson et al., "Separation of a Bioactive Cyclic Peptide and its Oligomeric Forms by Micellar Electrokinetic Chromatography", *Journal of Chromatography A* 769:301–306, 1997.

I. Björk et al., "Decreased Affinity of Recombinant Antithrombin for Heparin Due to Increased Glycosylation", *Biochem. Journal* 286:793–800, 1992.

L. Mourey et al., "Antithrombin III: Structural and Functional Aspects", *Biochimie* 72:599–608, 1990.

A. Bretnall et al., "Investigation and Optimisation of the Use of Organic Modifiers in Micellar Electrokinetic Chromatography", *Journal of Chromatography A* 716:49–55, 1995.

Y. Xu, "Capillary Electrophoresis", *Anal. Chem.* 65(12):425R–433R, 1993.

H. Nishi et al., "Chiral Separation of Diltiazem, Trimetoquinol and Related Compounds by Micellar Electrokinetic Chromatography with Bile Salts", *Journal of Chromatography* 515:233–243, 1990.

M. Evenson et al., "Automated Capillary Electrophoresis Applied to Therapeutic Drug Monitoring", *Clinical Chemistry* 38 (9):1847–1852, 1992.

R. Weinberger et al., "Micellar Electrokinetic Capillary Chromatography of Illicit Drug Substances", *Anal. Chem.* 63:823–827, 1991.

J. Noroski et al., "Determination of the Enantiomer of a Cholesterol–Lowering Drug by Cyclodextrin–Modified Micellar Electrokinetic Chromatography", *Journal of Pharmaceutical & Biomedical Analysis* 13 (1):45–52, 1995.

J. Jacquier et al., "Determination of Critical Micelle Concentration by Capillary Electrophoresis. Theoretical Approach and Validation", *Journal of Chromatography A* 718:167–175, 1995.

P. Hermentin et al., "A Strategy for the Mapping of N–Glycans by High Performance Capillary Electrophoresis", *Anal. Biochem.* 221:29–41, 1994.

M. Jaworska et al., "Capillary Electrophoretic Separation of N–Acetylcysteine and its Impurities as a Method for Quality Control of Pharmaceuticals", *Journal of Chromatography A* 853 (1–2):479–485, 1999.

O. Reif et al., "Control of the Cultivation Process of Antithrombin III and its Characterization by Capillary Electrophoresis", *Journal of Chromatography A* 680:383–394, 1994.

A. Buchacher et al., "High–Performance Capillary Electrophoresis for In–Process Control in the Production of Antithrombin III and Human Clotting Factor IX", *Journal of Chromatography A* 802:355–366, 1998.

W. Werner et al, "size–Dependent Separation of Proteins Denatured in SDS by Capillary Electrophoresis Using a Replaceable Sieving Matrix", *Anal. Biochem.* 212:253–258, 1993.

S. Rabel et al., "Applications of Capillary Electrophoresis in Pharmaceutical Analysis", *Pharmaceutical Research* 10 (2):171–186, 1993.

*Primary Examiner*—David M. Naff
*Assistant Examiner*—Mike Meller
(74) *Attorney, Agent, or Firm*—Finnegan, Henderson, Farabow, Garrett & Dunner, L.L.P.

(57) ABSTRACT

A process is disclosed for the baseline separation of the α and β variants of antithrombin III AT-III. The process involves subjecting a sample comprising AT III to cyclodextrin-modified micellar electrokinetic chromatography (CD-MEKC). The CD-MEKC is performed with a buffer comprising boric acid, an anionic tensid, β-cyclodextrin, and an aliphatic diamine at a basic pH. The CD-MEKC results in the separation of the AT III into AT III α and ATIII β. The anionic tensid can be sodium dodecyl sulfate and the aliphatic diamine can be 1, 5-diaminopentane.

34 Claims, 1 Drawing Sheet

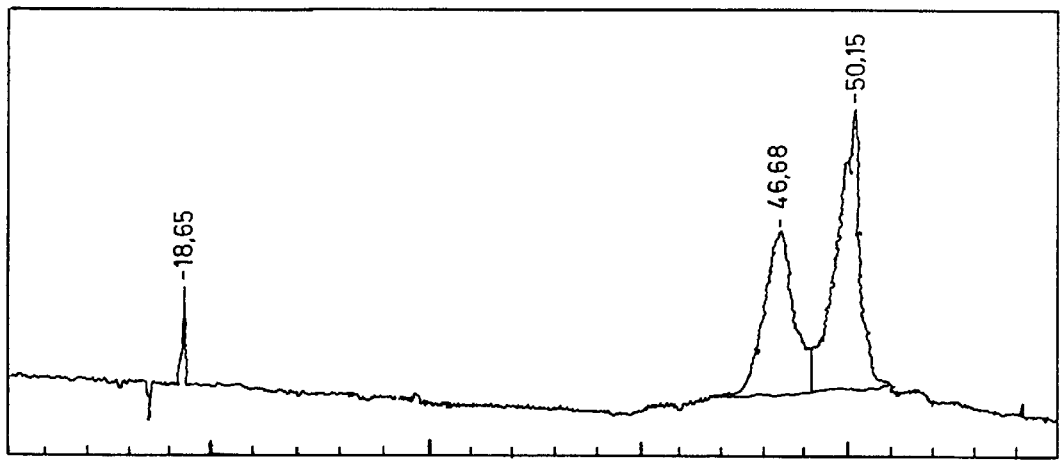

Fig.1a CZE analysis of a mixture of AT-III alpha and beta, 1mg/ml. Buffer: 50mM Sodium phosphate, pH7. Instrument: PE Applied Biosystems 270A-HT. Capillary: 72cm x 50μm I.D. Detection Wavelength: 200 nm. Voltage: 20kV, Current 33 μA. Oven Temperature: 30°C. Injection: 0,5 sec. Vacuum 169 mbar.

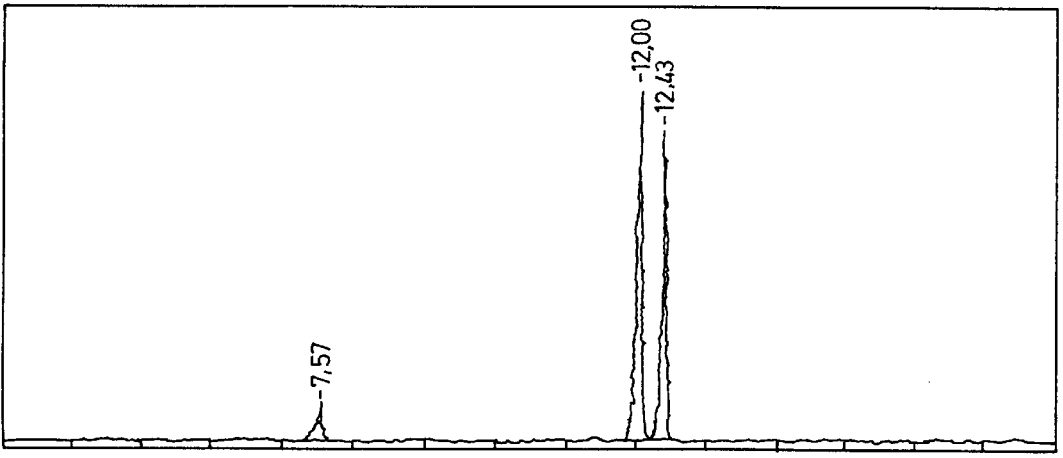

Fig.1b CD-MECK analysis of a mixture of AT-III alpha and beta, 1mg/ml. Buffer: 60mM Borate, 40mM SDS, 20mM beta-cyclodextrin, 1mM Di-aminopentane, pH9. Instrument: PE Applied Biosystems 270 A-HT. Capillary: 72cm x 50μm I.D. Detection wavelength: 200 nm. Voltage: 20kV, Current: 22μA. Oven temperature: 30°C. Sample injection: 0,5sec. Vacuum 169mbar.

SEPARATION OF ANTITHROMBIN III α AND β VARIANTS BY CYCLODEXTRIN-MODIFIED MICELLAR ELECTROKINETIC CHROMATOGRAPHY

BACKGROUND OF THE INVENTION

1. Field of the Invention

The present invention relates to the field of protein purification. In particular, the subject of the present application is a process for a baseline separation of the antithrombin III variants α and β.

2. Description of Related Art

One of the most challenging analytical tasks in modern bioanalysis is still the separation and characterization of proteins and peptides. The difficulties mainly derive from the complex structure of proteins, requiring several analytical techniques to get sufficient information. Conventionally used methods for protein separation are SDS-PAGE, SEC, MS, RP-HPLC etc. (ref. 1).

Although several modes of high performance liquid chromatography are well established, capillary electrophoresis (CE) and its different modes, namely capillary zone electrophoresis (CZE), SDS molecular weight capillary electrophoresis, capillary isoelectric focusing (CIEF), capillary gel electrophoresis (CGE), and last, but not least, micellar electrokinetic chromatography (MEKC) are rapidly gaining in acceptance (2).

Concerning the plasma glycoprotein antithrombin III (AT-III) which is responsible for thrombin inhibition in the blood coagulation cascade, a special analytical problem lies in the fact that it consists of two variants—the α- and the β-form—which are different in their affinity to the polysaccharide heparin. The availability of a reliable method to quantify AT-IIIα and β in, for example, plasma-derived concentrates and body fluids, will help to elucidate the currently not fully understood existence of the two isoforms.

In order to define the quality of AT-III, it is therefore meaningful to characterize it by the measurement of its portions of the α- and β-variants and to develop methods for their separation.

BRIEF DESCRIPTION OF THE DRAWING

FIG. 1 shows the results of analysis of AT-III using two different separation techniques.

A. Separation of AT-III α and β using CZE.

B. Separation of AT-III α and β using CD-MECK according to the present invention.

SUMMARY OF THE INVENTION

The problem of separating the AT-IIIα and AT-IIIβ isoforms is solved according to the present invention by a process for the baseline separation of the α-and β-variants of AT-III using Cyclodextrin micellar electrokinetic chromatography.

AT-III is a single chain plasma glycoprotein that inhibits most proteinases of the coagulation cascade, such as thrombin, which is its principal physiological target and thus plays a major role in the regulation of blood clotting. Inhibition of thrombin by AT-III occurs by the formation of a stable equimolar complex between inhibitor and protease. The rate of thrombin inactivation is enhanced by catalytic amounts of the sulfated polysaccharide heparin. Located in the N-terminal domain of the protein, the binding of heparin results in a conformational change in AT-III (refs. 3, 4).

The primary structure of human AT-III (antithrombin α) has a molecular weight of 58000 Da and an isoelectric point (pI) of 4.85.

In addition, it has been shown that there is also present an AT-III variant with increased heparin affinity which is called antithrombin β (molecular weight 55000 DA, pI=5.0), and which is deprived of a carbohydrate side chain.

Capillary electrophoresis (CE) combines the quantification and handling benefits of HPLC with the separating power of conventional electrophoretic techniques. As compared with HPLC, CE offers an important advantage, namely a wide variation of analytical conditions.

Free solution capillary electrophoresis, also called capillary zone electrophoresis (CZE), is the most common mode of capillary electroseparation, because it is performed in a capillary filled only with an electrolyte solution at a selected pH value and ionic composition. CZE is applicable to a wide range of charged substances, including pharmaceuticals, amino acids, peptides, and proteins. The separation in CZE is based on the differences in the electrophoretic mobilities, resulting in different velocities of migration of ionic species in the electrophoretic buffer contained in the capillary.

Whereas by CZE only ionic analytes are separated, in micellar electrokinetic chromatography (MEKC) an additional mechanism for selectivity is introduced. MEKC is a high-resolution technique using surfactant micelles to provide a charged vehicle which performs an electrophoretic separation of both neutral and charged solutes. Typically, anionic surfactants are included in the electrophoretic buffer (ref. 8).

Normally when surfactant molecules exceed their critical micelle concentration (CMC), micelles are formed in aqueous solution with the hydrophobic regions pointing inward and the hydrophilic heads pointing outward into the aqueous solution (ref. 6). The formation of micelles results in a pseudostationary phase created by the hydrophobic interior of the negatively charged micellar structure, which itself migrates towards the anode and therefore competes with the stronger electroendosmotic flow (EOF), which is towards the cathode. The sample molecules introduced into the EOF therefore distribute between the micelle and the electrophoretic buffer, whereas the separation rate is determined by both distribution and electrophoretic effects. Furthermore, differences in the distribution of charged and hydrophobic sites of the solute can strongly influence the separation, because solutes interact with micelles via various mechanisms including hydrophobic, electrostatic, and hydrogen bonding.

So MEKC is based on micellat solubilization and electrophoretic migration of the micelle. That is, the solutes are separated by the differential distribution between the micelle and the surrounding aqueous phase as well as the differential migration of the two phases. From the viewpoint of the separation principle, this analytical method can be classified as an individual tool of chromatographic technique, although it is performed with a capillary electrophoresis instrument (ref. 5).

Micellar electrokinetic separations in capillaries were first introduced by Terabe and have been extended by Sepaniak, Fujiwara, Honda, and others to pharmaceutical preparations (ref. 16).

The distribution of the solutes between micelles can be influenced by chiral selectors like cyclodextrins. Cyclodextrins (CDs) are oligosaccharides having 6–8 glucopyranose units connected in a ring. Their cyclic structure gives them a hydrophobic cavity. Solutes can enter these cavities, forming an inclusion complex. The addition of small amounts of chiral additives to the MEKC buffer, which leads to a special separation method called Cyclodextrin-modified micellar electrokinetic chromatography (CD-MEKC), seems to have several consequences, the most important being a change induced by stereospecific interactions to the distribution of the analyte between the micelle and the aqueous buffer phase (ref. 10). The chiral selectivity process is in competition with micellar inclusion and distribution, thus CDs are added to the MEKC electrolyte to reduce the retention of hydrophobic solutes and to stabilize the selectivity.

The choice of the run buffer is a consideration in separating proteins using CE. Typically, the type of buffer, its ionic strength, and its pH-value are adjusted for each compound to be separated based on various properties of the compound.

Whereas the separation of small peptides in the CZE mode is well established, it appears that no single strategy is applicable for large peptides and proteins. This is due largely to the complexity and diversity associated with these biomolecules. In solution, proteins exhibit acid-base behavior, and their net charge is dependent on the pH of the buffer. The net charge is zero at the characteristic isoelectric point (pI) where the number of positive charges is balanced precisely by the number of negative charges. Working above and below the pI value, which is nearly 5 for AT-III, will change the solute charge and cause the solute to migrate either before or after the EOF.

At a buffer pH of approximately 3, the AT-III possesses a positive charge and comigrates with the suppressed EOF towards the cathode. In this case, when working with low pH conditions, the capillary wall is protonated while the AT-III molecules are positively charged, thus minimizing the electrostatic adsorption on the capillary wall. At an acidic buffer pH, the EOF is very low and the AT-III molecules are mainly forced to move towards the cathode by their positive charge.

At basic pH, whereas the pI of the AT-III is less than the pH of the buffer, the electrophoretic mobility is towards the anode. At high pH, a relatively high EOF is generated. The predominating EOF prevents the negatively charged AT-III from migrating back off the capillary and carries the solute towards the cathode, passing the detector window just before reaching the cathodic side. Both the AT-III and the capillary wall are negatively charged and the adsorption process is minimized as a result of a charge repulsion effect.

DETAILED DESCRIPTION OF THE INVENTION

It has now been found that the process for a baseline separation of the antithrombin variants $\alpha$ and $\beta$ by means of Cyclodextrin-modified micellar electrokinetic chromatography gives excellent results if it is performed in the presence of a buffer solution comprising boric acid, an anionic tensid, $\beta$-cyclodextrin, and an aliphatic diamine at a basic pH value, such as between pH 8 and 10.

In one embodiment, the buffer solution contains boric acid, an anionic tensid, $\beta$-cyclodextrin, and, an aliphatic diamine. The boric acid can be present in the buffer in an amount of 40 to 80 mMol/l. The anionic tensid can be sodium-dodecylsulfate. The anionic tensid can be present in the buffer in an amount of 20 to 60 mMol/l, while the $\beta$-cyclodextrin can be present in an amount of 10 to 30 mMol/l. The aliphatic diamine can be 1,5-diaminopentane. The aliphatic diamine can be present in the buffer in an amount of 0.5 to 5 mMol/l.

While not wishing to be bound by a particular theory, it is believed that the borate anion resulting from addition of boric acid, might aid in separation by forming a complex with vicinal hydroxyl groups under alkaline conditions. Thus, it might play a role in stereoselective interactions (ref. 11).

The $\alpha$ and $\beta$ variants of AT-III have similar size-to-charge ratios, making their electrophoretic mobilities very similar. Separation can be facilitated by addition of an anionic surfactant, like sodium dodecylsulfate (SDS), to enhance selectivity through hydrophobic and electrostatic interactions with the micelles being introduced. Hydrophobic interactions play a major role in defining the native tertiary structure of proteins, because proteins consist of polar and non-polar amino acids. Typical recommended surfactant concentrations in MEKC are between 20 and 50 mM. Increasing the surfactant concentration increases the retention time, as a consequence of the interaction with the increased number of micelles.

In order to successfully separate the AT-III variants $\alpha$ and $\beta$ from each other, the present invention provides a CD-MEKC method based on borate as the basic buffer substance. In this embodiment, SDS acts as an anionic surfactant and $\beta$-cyclodextrin can be added to improve selectivity behavior. Furthermore, a small amount of an aliphatic diamine, such as the cationic 1,5-diaminopentane, can be added to prevent adsorption effects between solute and capillary wall.

It is to be noted that the critical micelle concentration (CMC), which is 8 mM for the most frequently used surfactant SDS, plays a role in MEKC. Below the CMC, which by the way decreases with the length of the alkyl chain of the particular surfactant molecule, the sample solubility will remain virtually the same as it is without a surfactant. Nevertheless the distribution of the monomeric surfactant molecules should not be neglected, because, especially in the case of CD-MEKC analysis, SDS monomers can have their hydrophobic tails co-included in the cyclodextrin cavity along with the analyte. Concerning the previously mentioned potential adsorption effects, use of SDS is advantageous because the ionic repulsion between the hydrophilic moieties of the surface-active molecules and the silanol groups seems to be strong enough to prevent any adsorption, and thus the zeta potential remains constant (ref. 7).

High efficiencies and a simple, straightforward process are two advantages of using chiral surfactants in the MEKC mode over the traditional HPCE methods. Through the addition of micelle-forming surfactants (such as SDS) and inclusion-forming compounds (such as $\beta$-cyclodextrin) to the HPCE electrolyte, a dynamic distribution mechanism is established. As optimal conditions for the CE separation are protein specific, the present fast and inexpensive method demonstrates that CD-MEKC can be successfully applied to the resolution and quantitation of the AT-III variants $\alpha$ and $\beta$.

The results of the separation process according to the invention are shown as follows:

A mixture containing approximately equal amounts of the AT-III variants $\alpha$ and $\beta$ was used.

Using customary free zone electrophoresis, the $\alpha$- and $\beta$-variants of AT-III were not properly resolved. At the end of the separation attempt, two broad peaks were obtained, but only after a rather long analysis time. This separation is demonstrated by FIG. 1a.

It was determined according to the present invention that only the use of aqueous solutions containing micelles and cyclodextrins as moving phases in capillary electrophoresis facilitated a separation, which provided a high resolution, resulting in two baseline separated peaks (FIG. 1b). It appeared that this selectivity was mainly based upon the interaction of the analyte with the micelle, whereas the cyclodextrin played a supporting role. And among the most commonly employed inorganic salts in MEKC, borate was the most appropriate for the present application.

Using the CD-MEKC buffer system according to the invention, a separation voltage of 20 kV, resulting in a current of less than 30 $\mu$A, could be applied without excessive Joule heating. Both compounds, AT-III $\alpha$ and AT-III $\beta$, exhibited excellent peak shape. The migration order was found to be $\alpha$ followed by $\beta$. Interpreting the migration order, the SDS micelles thus appear to have interacted more effectively with the $\beta$ variant, which is of smaller size. This corresponds to previous experiences that show that MEKC is more suitable for smaller proteins because larger proteins are less prone to penetrate into micelles. Certainly, the hydrophobicity of some proteins increases as their size increases, but the migration normally found is in the order of increasing size. Thus, the migration order makes sense because the interaction of solute and surfactant is the dominating separation mechanism concerning the present invention. Here, the interaction of the analyte with the cyclodextrin cavity appears to be of minor importance. $\beta$-cyclodextrin, which can influence the distribution of the solutes between micelles, acts to stabilize the separation process and enhance the resolution. This is true, for example, in the case of plasma derived samples.

The isoelectric points of AT-III (pI 4.8–5.1) and the molecular mass of the AT-III variants ($M_r$55,000 and 58,000, respectively) are close to those of human serum albumin (pI 4.9, $M_r$67,000). In further experiments, it was shown that plasma proteins like albumin, which can interfere with the AT-III analysis, were solubilized by the micelles employed. Thus, in agreement with the separation principle explained above, albumin eluted later than the AT-III variants.

Plasma sample impurities of smaller size, which are able to absorb UV light, elute much earlier than AT-III. Moreover, plasma samples of lower AT-III concentration, for example 0.1 mg/ml, have also been analyzed directly. They require a longer injection time, and therefore a reduced migration time. A pretreatment of the plasma sample is not necessary, which is of great advantage.

From all the data presented, it can be seen that this separation technique is of significance for the differentiation of AT-III variants $\alpha$ and $\beta$. The reproducibility within a series of runs was found to be improved by automatically changing the run buffer on the autosampler side of the PE Applied Biosystems 270A-HT instrument more frequently (up to ten injections per run buffer vial). Concerning the same fact, the second instrument used within the present application, namely the HP$^{3D}$CE system, is equipped with an automated buffer replenishment station, which can access any vial before or during an analysis, and empty and refill it with fresh buffer from a large volume reservoir, thus improving the reproducibility by avoiding buffer depletion situations.

The following example is provided to more fully explain an embodiment of the present invention. It is not intended to limit, and should not be interpreted as limiting, the invention in any way.

EXAMPLE

A buffer solution was prepared by dissolving first 0.37 g boric acid, 1.15 g SDS, 2.27 g $\beta$-cyclodextrin, and 12 $\mu$l 1,5-diaminopentane in approximately 90 ml Milli-Q water (Waters Millipore). The resulting solution was adjusted to pH 9 with 1 M sodium hydroxide. Finally the volume was completed to 100 ml, which result in the following buffer system:

60 mM boric acid 40 mM sodium dodecylsulfate 20 mM $\alpha$-cyclodextrin 1 mM diaminopentane adjusted to pH 9.

The buffer solution was usually stored at 2 to 8° C. Prior to use the solution was warmed up to room temperature and filtered through a 0.2 micron filter. As far as possible, practical, or desired, the solution should be degassed in order to prevent spikes in the electropherogram.

Unless otherwise indicated, the instrumentation used for the measurements reported herein was a PE Applied Biosystems 270A-HT Capillary Electrophoresis System, equipped with a monochromatic UV detector. Detection in CE is a significant challenge as a result of the small dimensions of the capillary and the nanoliter sample volumes. An adequate sample concentration of about 1 mg/ml, but not less than 0.1 mg/ml in the case of AT-III samples, is therefore suitable, presuming an ideal injection time of 0.5 seconds and 5 second response, corresponding to a volume of approximately 0.5 nanoliters (nl) and 5 nl, respectively. In view of the fact that higher wavelengths give lower sensitivity and that most CZE and MEKC buffers do not absorb at low wavelengths, 200 nm was used for general purpose detection (ref. 13).

A benefit of the air thermostating system used in the PE Applied Biosystems HPCE system is instrumental simplicity and ease of use. Further the system isolates the meandering installed capillary from changes in ambient temperatures. In consideration of the so called critical micelle temperature (CMT) in MEKC, where an increasing number of the monomeric surfactant molecules go into solution as the temperature is increased, the capillary was thermostatted at 30° C. This oven temperature, also proposed by the manufacturer, proved to be a satisfactory condition.

In HPCE, smaller diameter capillaries (25 $\mu$m) arre more effective at heat dissipation, but give reduced sensitivity with UV-detection because of the reduced path length. On the other hand enlarging the inner diameter to 75 $\mu$m leads to a decrease in resolution. So from heat dissipation and resolution perspectives, the use of a fused silica capillary with an inner diameter of 50 $\mu$m is advantageous. From an analysis time perspective, capillaries as short as possible should be used, but this is often in contrast to a good resolution. Longer capillaries can produce the separation of more components. But this necessarily contributes to a band broadening because of longer separation times. So the capillary length needs to be adapted on the specific separation.

Unless otherwise indicated, a polymide-coated fused silica capillary, 72 cm (50 cm effective length, respective to the detector)×50 $\mu$m I.D.×363 $\mu$m O.D. (Supelco, Bellefonte, Pa., USA) was used in the present application. The detection window was created by glowing off the polymide-coating using a CE Capillary Burner (Elektrokinetic Technologies, Broxburn, UK).

Prior to use, a brand-new capillary was equilibrated with 1 M sodium hydroxide for 30 minutes, with 0.1 M sodium hydroxide for 15 minutes, and finally with Milli-Q water. All flushing solutions were degassed properly using vacuum pump equipment. Between individual runs and before each injection response, the capillary was rinsed with Milli-Q water for 2 minutes, with 0.1 M sodium hydroxide for 2 minutes, and with the separation buffer for 6 minutes to prepare the capillary for the immediate separation. Concerning the storage of the capillary used for this specific separation, flushing the capillary with Milli-Q water for 10 minutes and then flushing from an empty vial for 5 minutes was the standard practice. The second rinse filled the capillary with air and prepared the capillary for a dry storage without plugging.

All samples were introduced at the anode side of the capillary by vacuum injection, using a 169 mbar vacuum (5-inch), applied injection time as mentioned above. A constant separation voltage of 20 kV was applied, generating a current of 22 $\mu$A for the CD-MEKC runs. Data collection was recorded via a Perkin Elmer 900 series interface. All peak information (migration time, peak area and height, as well as the area percent values) was obtained through the Nelson PC-integrator software version 5.1.

The robustness of the separation method was finally tested by using a HPCE instrument of another manufacturer. A comparison shows that the results achieved with the HP$^{3D}$CE instrument (Hewlett Packard) are in a good agreement with those obtained with the ABI 270A-HT instrument (Perkin Elmer), although the operational conditions are slightly different in consequence of construction and functioning of the instruments.

The HP$^{3D}$CE system is also a versatile, fully automated system which houses a high-voltage power supply, a carousel for autosampling, a constantly pressure controlled injection system, an on-capillary high-sensitivity diode array detector, a buffer replenishment station, and a capillary cartridge, thermostatted through a high-velocity air flow regulated by a Peltier element. The HP$^{3D}$CE ChemStation comprises instrument control and data handling software.

For analyses carried out with the HP$^{3D}$CE system, the capillary length was 70 cm (61.5 cm effective length). Furthermore the samples were loaded by using an injection pressure of 50 mbar. Injection time was 1 second presuming an AT-III sample concentration of 1 mg/ml.

References (1) Eva Szökö, "Protein and peptide analysis by capillary zone electrophoresis and micellar electrokinetic chromatography" Electrophoresis 18 (1997) 74–81.
(2) Maria Petersson, Karin Walhagen, Anders Nilsson, Karl-Gustav Wahlund, Staffan Nilsson "Separation of a bioactive cyclic peptide and its oligomeric forms by micellar electrokinetic chromatography" Journal of Chromatography A 769 (1997) 301–306.
(3) Ingernar Björk, Karin Ylinenjärvi, Steven T. Olson, Peter Hermentin, Harald S. Couradt and Gerd Zettlmeissl "Decreased affmity of recombinant antithrombin for heparin due to increased glycosylation" Biochem. Journal 286 (1992) 793–800.
(4) L Mourey, JP Samama, NI Delarue, J Choay, JC Lormeau, M Petitou, D Moras "Antithrombin III: structural and functional aspects" Biochimie 72 (1990) 599–608.
(5) Alison E. Bretnall, Graham S. Clarke "Investigation and optimisation of the use of organic modifiers in micellar electrokinetic chromatography" Journal of Chromatography A 716 (1995) 49–55.
(6) Yan Xu "Capillary Electrophoresis" Analytical Chemistry Vol. 65, No. 12 (1993) 425–433.
(7) Hiroyuld Nishi, Tsukasa Fukuyama, Masaaki Matsuo and Shigeru Terabe "Chiral Separation of diltiazem, trimetoquinol and related compounds by micellar electrokinetic chromatography with bile salts" Journal of Chromatography 515 (1990) 233–243.
(8) Merle A. Evenson and John E. Wiktorowicz "Automated Capillary Electrophoresis Applied to Therapeutic Drug Monitoring" Clinical Chemistry Vol. 38, No.9 (1992) 1847–1852.
(9) Robert Weinberger, Ira S. Lurie "Micellar Electrokinetic Capillary Chromatography of Illicit Drug Substances" Analytical Chemistry 63 (1991) 823–827.
(10) J. E. Noroski, D. J. Mayo and M. Moran "Determination of the enantiomer of a cholesterol-lowering drug by cyclodextrin-modified micellar electrokinetic chromatography" Journal of Pharmaceutical & Biomedical Analysis Vol. 13, No. 1 (1995) 45–52.
(11) J. C. Jacquier, P. L. Desbene "Determination of critical micelle concentration by capillary electrophoresis. Theoretical approach and validation" Journal of Chromatography A 718 (1995) 167–175.
(12) P. Hermentin, R. Doenges, R. Witzel, C. H. Hokke, J. P. K. Vliegenthart, H. S. Conradt, M. Nirntz, and D. Brazel "A Strategy for the Mapping of N-Glycans by High Performance Capillary Electrophoresis" Analytical Biochemistry 221 (1994) 29–41.
(13) Mallgorzata Jaworska, Zofia Szulinska, Malgorzata Wilk, Jadwiga Tautt "Capillary electrophoretic separation of N-acetylcysteine and its impurities as a method for quality control of pharmaceuticals" Journal of Chromatography A Vol. 853, No. 1–2 (1999) 479–485.
(14) Oscar-Werner Reif, Ruth Freitag "Control of the cultivation process of antithrombin III and its characterization by capillary electrophoresis" Journal of Chromatography A 680 (1994) 383–394.
(15) Andrea Buchacher, Petra Schulz, Jacek Choromanski, Horst Schwinn, Djuro Josic "High-performance capillary electrophoresis for in-process control in the production of antithrombin III and human clotting factor IX" Journal of Chromatography A 802 (1998) 355–366.
(16) William E. Werner, David M. Demorest, Junko Stevens, and John E.

Wiktorowicz "Size-Dependent Separation of Proteins Denatured in SDS by Capillary Electrophoresis Using a Replaceable Sieving Matrix" Analytical Biochemistry 212 (1993) 253–258.
(17) Shelley R. Rabel and John F. Stobaugh "Applications of Capillary Electrophoresis in Pharmaceutical Analysis" Pharmaceutical Research Vol. 10, No. 2 (1993) 171–186.

What is claimed is:

1. A process for separation of antithrombin III α (ATIIIα) and antithrombin III β (ATIIIβ), said process comprising
    subjecting a sample comprising antithrombin III (ATIII) to cyclodextrin-modified micellar electrokinetic chromatography (CD-MEKC),
    wherein the CD-MEKC is performed with a buffer comprising boric acid, an anionic tensid, β-cyclodextrin, and an aliphatic diamine, at a basic pH,
    wherein the CD-MEKC results in separation of the ATIII into ATIIIα and ATIIIβ.

2. The process of claim 1, wherein the boric acid is present in the buffer at a concentration of 40 to 80 mM.

3. The process of claim 2, wherein the boric acid is present in the buffer at a concentration of 60 mM.

4. The process of claim 1, wherein the anionic tensid is sodium dodecyl sulfate (SDS).

5. The process of claim 4, wherein the SDS is present in the buffer at a concentration of 8 to 60 mM.

6. The process of claim 1, wherein the anionic tensid is present in the buffer at a concentration of 20 to 60 mM.

7. The process of claim 5, wherein the anionic tensid is present in the buffer at a concentration of 20 to 50 mM.

8. The process of claim 5, wherein the anionic tensid is present in the buffer at a concentration of 40 mM.

9. The process of claim 1, wherein the β-cyclodextrin is present in the buffer at a concentration of 10 to 30 mM.

10. The process of claim 9, wherein the β-cyclodextrin is present in the buffer at a concentration of 20 mM.

11. The process of claim 1, wherein the aliphatic diamine is 1,5-diaminopentane.

12. The process of claim 1, wherein the aliphatic diamine is present in the buffer at a concentration of 0.5 to 5 mM.

13. The process of claim 12, wherein the aliphatic diamine is present in the buffer at a concentration of 1 mM.

14. The process of claim 1, wherein the pH of the buffer is between 8 and 10.

15. The process of claim 1, wherein the pH of the buffer is 9.

16. The process of claim 1, wherein the sample is plasma.

17. The process of claim 16, wherein the plasma is not treated before subjecting it to CD-MEKC.

18. The process of claim 1, wherein the concentration of ATIII in the sample is 0.1 to 1.0 mg/ml.

19. A process for separation of antithrombin III α (ATIIIα) and antithrombin III β (ATIIIβ), said process comprising subjecting a sample comprising antithrombin III (ATIII) to cyclodextrin-modified micellar electrokinetic chromatography (CD-MEKC),
wherein the CD-MEKC is performed with a buffer comprising
boric acid at a concentration of 40 to 80 mM,
an anionic tensid at a concentration of 20 to 60 mM,
β-cyclodextrin at a concentration of 10 to 30 mM, and
an aliphatic diamine at a concentration of 0.5 to 5 mM,
wherein the buffer has a pH of 8–10,
wherein the CD-MEKC results in separation of the ATIII into ATIIIα and ATIIIβ.

20. The process of claim 19, wherein the anionic tensid is SDS.

21. The process of claim 19, wherein the aliphatic diamine is 1,5-diaminopentane.

22. The process of claim 19, wherein the boric acid is present in the buffer at a concentration of 60 mM.

23. The process of claim 19, wherein the anionic tensid is present in the buffer at a concentration of 20 to 50 mM.

24. The process of claim 23, wherein the anionic tensid is present in the buffer at a concentration of 40 mM.

25. The process of claim 19, wherein the β-cyclodextrin is present in the buffer at a concentration of 20 mM.

26. The process of claim 19, wherein the aliphatic diamine is present in the buffer at a concentration of 1 mM.

27. The process of claim 19, wherein the pH of the buffer is 9.

28. The process of claim 19, wherein the sample is plasma.

29. The process of claim 28, wherein the plasma is not treated before subjecting it to CD-MEKC.

30. The process of claim 19, wherein the concentration of ATIII in the sample is 0.1 to 1.0 mg/ml.

31. A process for separation of antithrombin III α (ATIIIα) and antithrombin III β (ATIIIβ), said process comprising
subjecting a sample comprising antithrombin III (ATIII) to cyclodextrin-modified micellar electrokinetic chromatography (CD-MEKC),
wherein the CD-MEKC is performed with a buffer comprising
boric acid at a concentration of 60 mM,
SDS at a concentration of 40 mM,
β-cyclbdextrin at a concentration of 20 mM, and
1,5-diaminopentane at a concentration of 40 mM,
wherein the buffer has a pH of 9,
wherein the CD-MEKC results in separation of the ATIII into ATIIIα and ATIIIβ.

32. The process of claim 31, wherein the sample is plasma.

33. The process of claim 32, wherein the plasma is not treated before subjecting it to CD-MEKC.

34. The process of claim 31, wherein the concentration of ATIII in the sample is 0.1 to 1.0 mg/ml.

* * * * *

UNITED STATES PATENT AND TRADEMARK OFFICE
CERTIFICATE OF CORRECTION

PATENT NO.   : 6,395,881 B1
DATED        : May 28, 2002
INVENTOR(S)  : Reiner Doenges et al.

It is certified that error appears in the above-identified patent and that said Letters Patent is hereby corrected as shown below:

Column 9,
Line 25, "0. 1" should read -- 0.1 --.

Column 10,
Line 31, "β-cyclbdextrin" should read -- β-cyclodextrin --.
Line 32, "40 mM" should read -- 1 mM --.

Signed and Sealed this

Twenty-fifth Day of February, 2003

JAMES E. ROGAN
*Director of the United States Patent and Trademark Office*